(12) United States Patent
Lawson et al.

(10) Patent No.: US 7,771,969 B2
(45) Date of Patent: Aug. 10, 2010

(54) METHODS FOR OBTAINING ANTIBODIES (75) Inventors: Alastair David Griffiths Lawson, Slough (GB); Meryn Ruth Griffiths, Slough (GB)

(73) Assignee: Celltech R&D Limited, Slough (GB)

( * ) Notice: Subject to any disclaimer, the term of this patent is extended or adjusted under 35 U.S.C. 154(b) by 768 days.

(21) Appl. No.: 10/568,377

(22) PCT Filed: Aug. 12, 2004

(86) PCT No.: PCT/GB2004/003491

§ 371 (c)(1), (2), (4) Date: Sep. 14, 2006

(87) PCT Pub. No.: WO2005/019823

PCT Pub. Date: Mar. 3, 2005

(65) Prior Publication Data

US 2007/0009508 A1    Jan. 11, 2007

(30) Foreign Application Priority Data

Aug. 20, 2003 (GB) ................... 0319587.2
Feb. 6, 2004 (GB) ................... 0402642.3

(51) Int. Cl.
*C12N 5/06* (2006.01)
*C12P 21/08* (2006.01)

(52) U.S. Cl. .................. 435/69.6; 435/70.4; 435/70.21; 435/326

(58) Field of Classification Search ....................... None
See application file for complete search history.

(56) References Cited

U.S. PATENT DOCUMENTS

| 5,786,161 A | 7/1998 | Irsch et al. |
| 6,875,599 B2 * | 4/2005 | Lazdunski et al. .......... 435/198 |

FOREIGN PATENT DOCUMENTS

| EP | 0488470 A1 * | 6/1992 |
| WO | WO 92/02551 | 2/1992 |
| WO | WO 94/09117 | 4/1994 |
| WO | WO 99/58977 | 11/1999 |
| WO | WO 02/057423 | 7/2002 |
| WO | WO 2004/051268 | 6/2004 |

* cited by examiner

Primary Examiner—David A Saunders (57) ABSTRACT

The invention is directed towards a method of enriching a population of cells in those cells that produce an antibody which recognises an antigen of interest. In particular, an untagged antigen is used in conjunction with a polyclonal antibody to isolate cells recognizing said antigen.

2 Claims, 1 Drawing Sheet

METHODS FOR OBTAINING ANTIBODIES

CROSS REFERENCE TO RELATED APPLICATIONS

The present application is a National Stage Application claiming the priority of co-pending PCT Application No. PCT/GB2004/003491 filed Aug. 12, 2004, which in turn, claims priority from Great Britain Application Serial No. 0319587.2 filed Aug. 20, 2003 and Great Britain Application Serial No. 0402642.3 filed Feb. 6, 2004. Applicants claim the benefits of 35 U.S.C. §120 as to the PCT application and priority under 35 U.S.C. §119 as to the said Great Britain applications, and the entire disclosures of all applications are incorporated herein by reference in their entireties.

The present invention relates to improved methods for the selection of cells producing antibodies specific for an antigen of interest.

Antibodies are a particular class of proteins which have been developed for therapeutic and diagnostic purposes. The isolation of cells producing antibody specific for an antigen of interest is historically performed using hybridoma technology. Other methods include isolating antibodies from bacterially expressed libraries which are limited by: (i) restrictions to the practical limits of the size of libraries; and (ii) the requirement for the antibody to be expressed and properly folded in bacteria. A number of alternative methods have been designed to enable high affinity antibodies generated during in vivo immune responses to be isolated from any species (Babcook et al., 1996, Proc. Natl. Acad. Sci, 93, 7843-7848; WO 92/02551; de Wildt et al., 1997, J. Immunol. Methods, 207:61-67 and in Lagerkvist, et al., 1995, BioTechniques 18(5):862-869).

Methods for the detection and isolation of cells producing antibody specific for an antigen of interest are well-known in the art and include isolation of antibody producing cells by binding to biotinylated antigen and capture on streptavidin-beads, panning against antigen-coated plastic surfaces, rosetting with antigen-coated red blood cells, flow cytometric analysis and single cell sorting where the antigen is fluorescently labelled. The major drawback of these methods is that the presentation of antigen is generally random such that masking of the antigenic epitope, which is specifically recognised by the antibody producing cell, can occur. In particular, where the antigen of interest is a protein, the labelling of the antigen for example with a fluorescent label, is a chemical modification of the surface of the antigen that can decrease the affinity of an antibody-antigen interaction or prevent interaction. Where the antigens of interest are small proteins or short peptides the introduction of a chemical modification in the form of a label, such as a fluorescent label, may interfere such that little or no binding of antigen to specific antibody occurs.

Similar problems exist where the antigen of interest is provided tagged as a fusion protein. The incorporation of an additional sequence on the C-terminus or N-terminus of a protein can result in aberrant folding such that the antigen is not folded into a native conformation. As such antigenic epitopes exposed within, for example, a host immunised with native antigen may not be accessible on a fusion protein of the same antigen. Thus, at the step of enrichment of cells producing antibody specific for the native antigen, those cells producing antibody to epitopes which are masked or altered in the fusion protein will not be detected and isolated.

Using unlabelled or untagged antigen is therefore particularly advantageous in that this avoids any modification of the antigen which can modify or mask interaction sites and which, in turn, can result in absence of detection of an antibody specific for the antigen of interest. Accordingly, provided is a method of obtaining from a population of cells those cells which produce an antibody which recognises an antigen of interest, said method comprising:

a) bringing into contact:
  i) a population of cells at least one of which is capable of producing an antibody;
  ii) an antigen of interest;
  iii) an antibody-particle complex wherein said antibody recognises an antigen of interest and said particle enables recovery of said complex; and
b) recovering from the population those cells associated with the antibody-particle complex.

It will be apparent to one skilled in the art that the methods can be performed in various permutations. Thus, for example parts i) to iii), above, can be performed simultaneously. In another embodiment, the population of part i) is brought into contact with the antigen of part ii), optionally followed by at least one wash step, followed by contact with the complex of part iii). In a further embodiment, the antigen of part ii) is brought into contact with the complex of part iii), optionally followed by at least one wash step, followed by contact with the population of part i).

Thus, in one embodiment, provided is a method of enriching a population of cells in those cells which produce an antibody which recognises an antigen of interest, comprising bringing an antibody-particle complex wherein the antibody recognises an antigen of interest into contact with the antigen of interest, to form an antigen-antibody-particle complex; bringing said antigen-antibody-particle complex into contact with a population of cells at least one of which is capable of producing an antibody; and separating from the population those cells associated with the antigen-antibody-particle complex, thus obtaining an enriched population associated with said complex.

In a preferred embodiment, the method of the invention additionally comprises a wash step after the formation of the antigen-antibody-particle complex, above. Most preferably, at least one wash step is performed after each contact has occurred.

Such wash steps can be performed in an appropriate buffer as known to one skilled in the art, for example phosphate buffered saline (PBS) or other appropriate medium. Recovery of complexes may be performed by any appropriate means, for example centrifugation, settling under gravity, filtration, or magnetic isolation. Preferably, the particles used are magnetic particles and recovery of antigen-antibody-particle complexes from any suspension and/or wash buffer or other medium is achieved by virtue of the particle being capable of being isolated using a magnet. For example but without limitation, antigen-antibody-particle complexes may be placed in a tube with a magnet placed against said tube or at least partially surrounding the tube, or said complexes may be placed in a well with a magnet placed underneath said well. Any complexes not associated with a particle, or antigen or antibody not associated with a particle may be removed by removing the suspension buffer or other medium and any magnetically captured complexes may optionally be washed at least once in an appropriate buffer or other medium. It will be understood by one skilled in the art that recovery of antigen-antibody-particle complexes, wherein the particle is not magnetic, may also be performed in a similar manner, for example using a tube comprising a filter, e.g. a membrane, to retain said particles within the tube.

In a further embodiment, at least one wash step is performed after the performance of parts i) to iii), above. The one or more cells associated with the antibody-particle complex may be separated from any suspension media or wash media using, for example but without limitation, centrifugation, filtration or magnetic isolation. Alternatively, the complex may be left to settle under gravity followed by removal of the washing buffer or other media.

In a particular embodiment, provided is a method of enriching a population of cells in those cells which produce an antibody which recognises an antigen of interest, comprising bringing a population of cells at least one of which recognises an antigen of interest into contact with said antigen; contacting an antibody-particle complex wherein the antibody recognises the antigen of interest to form a complex comprised of an antibody producing cell, antigen, antibody recognising said antigen and a particle; and separating from the population those cells associated with the complex, thus obtaining an enriched population associated with said complex. Optionally, one or more wash steps can be performed after each contact step.

Thus, using the methods of the invention an enriched population of cells producing an antibody which recognises an antigen of interest can be obtained.

The terms 'cells which are capable of producing an antibody' or 'antibody producing cell' include any cell secreting an antibody, such as a B-lymphocyte, a plasma cell, a plasmablast, an activated B cell or a memory B cell. Such cells may produce antibody of any affinity, for example high affinity antibody or lower affinity antibody. The methods of the invention are not dependent on the affinity of the antibody produced by such cells. A population comprising antibody producing cells for use in the invention may be obtained from an animal which has either been immunized with an antigen of interest, or which has developed an immune response to an antigen as a result of disease. For example but without limitation, the population can comprise a peripheral blood cell sample, spleen cells or cells derived from a lymph node. Other populations comprising antibody producing cells for use in the present invention may include a population of hybridoma cells, a population comprising any transformed cell, and in particular, a population comprising any mammalian cells which express immunoglobulin genes or parts thereof. Examples of such mammalian cells include but are not limited to NS0, CHO, COS and 293 cells. In a preferred embodiment, the populations of antibody producing cells for use in the present invention produce a range of antibodies with different binding specificities. As such, the methods of the invention are not dependent on the affinity of the antibody produced by said cells. In another embodiment, the population of cells comprising at least one cell producing an antibody which recognises an antigen of interest is derived from several sources, for example but without limitation from several lymph nodes which may be from one or more animals. It will also be apparent that samples or populations of cells derived from two or more animals can be pooled for use in the methods of the invention. In a particular embodiment, the population of cells is derived from a human who has been exposed to an antigen of interest or who has developed an immune response to an antigen as a result of a disease or condition. In such a case, the sample comprising the population of cells for enrichment is preferably a peripheral blood sample or one or more lymph nodes.

Preferably, the population is suspended in an appropriate medium for use in the methods of the invention. An appropriate medium for the assay will be one that provides at least the minimum requirements for short-term maintenance of cellular integrity and cellular structures, such as an isotonic buffer. One example, but without limitation, is immune cell medium comprising Roswell Park Memorial Institute medium (RPMI)+10% foetal bovine serum; 50 µM 2-β-mercaptoethanol; 2 mM glutamine; 20 mM Hepes; and 1× Penicillin and Streptomycin. Under such conditions the antibody producing cells produce and secrete antibodies.

A population comprising antibody producing cells may be depleted of unwanted cells such as for example but without limitation, red blood cells, T cells, macrophages or other cells if so desired. In the methods of the invention the population of cells provided, at least one of which is capable of producing an antibody, is preferably depleted of any red blood cells for example using centrifugation or red cell lysis as known in the art.

The particle for attachment to an antibody of part iii), above, to form an antibody-particle complex may be any suitable particle known in the art, for example a Sepharose-based or agarose-based particle, or a magnetic particle such as Dynabeads® (Dynal Biotech UK, The Wirral, UK), MACS® beads (Miltenyi Biotech Ltd, Surrey, UK) or other magnetic beads. Attachment of the antibody of part iii), above, to a particle may be achieved by means known in the art, such as by following the instructions provided by the manufacturer of the particle. Antibodies are preferably used at, for example but without limitation, 1-5 µg/ml and incubation of such antibodies with a particle comprising the particles for attachment is preferably performed as known in the art. It will be apparent to one skilled in the art that the concentration of antibody may be less or more than the stated values, above, and hence may range from, for example 0.1 µg/ml or less to 10 µg/ml or more. Most preferably, magnetic beads are used in the methods of the invention.

In a particular embodiment, the particle for attachment to an antibody of part iii), above, is a cell presenting on its surface an antigen of interest, i.e. the antigen of part ii), above. In this case the cell can be rendered magnetic, for example and without limitation, by ingestion of iron particles, or by biotinylation of the cell and capture via avidin-beads (e.g. avidin-linked magnetic beads). In a preferred embodiment, the particle for attachment to an antibody of part iii), above, is a cell presenting on its surface an antigen of interest (i.e. the antigen of part ii), above) and a second, different antigen to which is attached a magnetic bead via an antibody which is bound to said second antigen. The antigens of interest may be endogenous or recombinant, as may the second, different antigen.

The term 'antibody' as used herein includes any recombinant or naturally occurring immunoglobulin molecule such as a member of the IgG class e.g. IgG1, including a monoclonal or polyclonal antibody, any antigen binding immunoglobulin fragment, such as Fv, Fab' and F(ab')$_2$ fragments, and any derivatives thereof, such as single chain Fv fragments. The term antibody which 'recognises an antigen' includes an antibody which binds to or is specific for an antigen of interest. Most preferably, an antibody binds to the antigen of interest and does not bind to or recognise other unrelated antigens.

In the methods of the invention, the antibody of part iii) above is most preferably a polyclonal antibody which is from the same source as that of the population of cells for enrichment. In a preferred example the source of the population of cells is an animal immunised with an untagged antigen of interest and the polyclonal antibody is prepared from a sample of blood from said immunised animal. In another embodiment, the antibody of part iii) above is present in a pool of polyclonal sera; for example it is present in a pool of sera from at least two animals which have been immunised with the antigen of interest. It will be apparent to one skilled in the art that the polyclonal antibody may be present as a serum sample, but is more preferably prepared as an IgG fraction using means well known in the art. Methods for producing an IgG fraction are well known in the art and include affinity chromatography such as Protein A or Protein G affinity chromatography, and ammonium sulphate or caprylic acid precipitation. The polyclonal antibody may be a whole IgG or a fragment thereof such as a Fab', F(ab')$_2$ or Fab fragment. Fragments may be produced using any method known in the art, for example using papain or pepsin digestion. In an alternative embodiment, the antibody of part iii) above is a monoclonal antibody.

In the methods of the invention the antigen is provided in an untagged form. The term 'antigen' includes any substance that can be recognised by an antibody, including proteins, glycoproteins and carbohydrates. Preferably these antigens include biologically active proteins, such as hormones, cytokines, and their cell surface receptors, bacterial or parasitic cell membranes or purified components thereof, and viral antigens. Most preferably, the antigen is available in a pure form obtained either by direct purification from the native source or by recombinant expression and purification of said antigen. A pure form includes antigens which are at least 75%, 80%, 85% or 90% free from contaminants, and preferably at least 95% or 99% free from contaminants. Most preferably, antigens are 100% pure or have no detectable contaminants. In one embodiment, the antigen is expressed recombinantly as a fusion protein and the fusion tag has been removed prior to use of the antigen. Removal of such tags is well known in the art and such removal may leave a small number of residual amino acid residues which are not normally present at the N-terminus or C-terminus of the antigen in its native state, e.g. residues from a linker region and/or the region of cleavage of the tag. Thus, the term 'untagged' antigen includes antigens which have had a tag removed regardless of whether or not additional amino acid residues remain attached to the antigen as a result of the cleavage. Examples of such tags are known in the art and expression vectors incorporating nucleic acid code for such tags are commercially available for example, but not limited to, myc, FLAG or His tags.

Preferably, incubation of the antigen at a concentration of approximately 1 µM to 1 pM in the presence of a population of, for example but without limitation, approximately $10^7$ or $10^8$ white blood cells some of which are capable of producing antibody is performed on ice for approximately 60 min. It is understood that the number of cells may be less or more than $10^7$, and may be $10^6$, $10^5$, $10^4$ or less, or $10^9$ or more as desired. The concentration of antigen may also be varied and may be chosen as appropriate and understood by one skilled in the art. In one embodiment, low concentrations of antigen can be used to bias towards selecting B cells which produce high affinity antibody.

An enriched population of cells obtained using any of the methods of the invention may be further separated to obtain and clone one or more single antibody producing cells using any method known in the art. Methods to obtain and clone single antibody producing cells include methods such as, but not limited to, the selected lymphocyte antibody method (SLAM) described in WO 92/02551 and Babcook et al., 1996, Proc. Natl. Acad. Sci USA 93:7843-7848. Other techniques include those described by de Wildt et al., 1997, J. Immunol. Methods, 207:61-67 and Lagerkvist et al., 1995, BioTechniques 18(5):862-869. The above methods rely on the isolation of individual antibody producing cells which are then clonally expanded followed by screening for those clones which are producing an antibody which recognises an antigen of interest, and, if desired, the subsequent identification of the sequence of their variable heavy ($V_H$) and light ($V_L$) chain genes. Alternatively, the cells producing antibody which recognises an antigen of interest may be cultured together followed by screening and, if desired, sequence identification as above. In such a case, the enriched population of cells is divided such that a plurality of cells is placed in the well for culture. It is preferred that the wells are seeded with between 2 and 100 B cells; more preferably with between 2 and 75 B cells; more preferably between 5 and 50 B cells; more preferably between 5 and 25 B cells; more preferably between 5 and 15 B cells; more preferably between 8 and 12 B cells; yet more preferably about 10 B cells/well.

In one embodiment, the B cells are cultured for about, or at least, 4, 5, 6, 7, 8, 9 or 10 days or up to one month. Preferably, the B cells are cultured for about 5 to 10 days, more preferably for about 6 to 9, or 6 to 8 days.

Most preferably, the cells are cultured under conditions suitable for the clonal expansion of the B cells. Clonal expansion results in a greater quantity of antibody being produced and higher levels of mRNA expression. Clonal expansion is preferably performed in the presence of an antigen to which the antibody with the desired function binds which may assist in the isolation of higher affinity antibodies via in vitro affinity maturation.

Conditions suitable for the clonal expansion of B cells are well known in the art. Important conditions include the culture medium, the time for which the cells are cultured, temperature and atmospheric $CO_2$.

Preferably, the B cells are cultured with irradiated EL-4 cells in T cell conditioned media. More preferably, the B cells are cultured with irradiated mutant murine EL-4 thymoma cells, EL-4/B5, in conjunction with human T-cell/macrophage supernatant as a source of proliferation and differentiation factors. The EL-4/B5 cells activate the B-cells via a MHC-nonrestricted direct cell-cell interaction. The activation signal itself is not mitogenic but sensitizes the B cells to respond to one (IL-2) or several cytokines present in human T-cell supernatant.

Once the cells have been cultured, a plurality of the cultured cells may be screened to ascertain the presence of cells capable of producing an antibody having the desired function. Preferably, this involves screening the culture supernatant of said plurality of cultured cells.

Where cells have been cultured in a series of wells, the wells can be individually assayed (e.g. by taking culture supernatant from the wells) for the presence of cells capable of producing an antibody recognising the antigen of interest to thereby identify one or more wells which are positive for the presence of cells capable of producing an antibody having the desired function. Said antibodies can then be obtained from a positive well, e.g. by isolation. The antibodies can be obtained directly or indirectly from the cells present in the well.

Accordingly, also provided is a method of isolating an antibody which recognises an antigen of interest comprising:
a) bringing into contact:
  i) a population of cells at least one of which is capable of producing an antibody;
  ii) an antigen of interest;
  iii) an antibody-particle complex wherein said antibody recognises an antigen of interest and said particle enables recovery of said complex;
b) recovering from the population, those cells associated with the antibody-particle complex;
c) culturing a plurality of those cells associated with the antigen-antibody-particle complex;

d) screening the cultured cells to identify those cells capable of producing an antibody which recognises an antigen of interest; and e) isolating said antibody directly or indirectly from the cells.

Further provided is a method of isolating an antibody which recognises an antigen of interest comprising:

a) bringing an antibody-particle complex wherein the antibody recognises an antigen of interest into contact with the antigen of interest, to form an antigen-antibody-particle complex;

b) bringing said antigen-antibody-particle complex into contact with a population of cells at least one of which is capable of producing an antibody;

c) separating from the population those cells associated with the antigen-antibody-particle complex;

d) culturing a plurality of those cells associated with the complex;

e) screening the cultured cells to identify those cells capable of producing an antibody which recognises an antigen of interest; and f) isolating said antibody directly or indirectly from the cells.

Screening for cells producing antibodies recognising the antigen of interest may be performed by any means known in the art, such as by enzyme-linked immunosorbent assay (ELISA) or by screening for a functional activity such as neutralisation of antigen activity, or antagonistic or agonistic activities. Such assays are known in the art, for example, functional screening of receptor/ligand binding. Antibodies may be selected based on binding affinities such as, for example, may be determined using a BIAcore machine, or using a competitive radioimmunoassay.

The desired antibody, i.e. the antibody recognising the antigen of interest, may be isolated directly or indirectly from the cultured cells or from descendants thereof. Direct isolation can be achieved by purification of secreted antibody from the clonal culture supernatant using standard, well-known techniques, e.g. capture on Protein A or G beads, or precipitation. Alternatively, indirect isolation is performed. Such antibodies are produced by isolating the $V_L$ and $V_H$ chain gene regions or the entire genes may be cloned and used to produce recombinant antibodies which recognise the antigen of interest.

Such antibodies can include functionally active fragments, derivatives or analogues and may be, but are not limited to, bi-, tri- or tetra-valent antibodies, humanized or chimeric antibodies, single chain antibodies, Fab fragments, Fab' and Fab'2 fragments, fragments produced by a Fab expression library, anti-idiotypic (anti-Id) antibodies, epitope-binding fragments and derivatives of any of the above, e.g. single chain FV fragments. Humanized antibodies are antibody molecules from non-human species having one or more complementarity determining regions (CDRs) from the non-human species and a framework region from a human immunoglobulin molecule (see, e.g. U.S. Pat. No. 5,585,089). The methods for creating these antibody molecules are well known in the art (see for example, Boss et al., U.S. Pat. No. 4,816,397; Cabilly et al., U.S. Pat. No. 6,331,415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., 1983, Nature 305:537-539; WO 93/08829, Traunecker et al., 1991, EMBO J. 10:3655-3659). Bi-, tri- and tetra-valent antibodies may comprise multiple specificities or may be monospecific (see for example WO 92/22853).

The types of expression systems available to produce these antibody molecules include bacterial, yeast, insect and mammalian expression systems, the methods for which are well known in the art (Verma et al., 1998, Journal of Immunological Methods, 216, 165-181). Techniques for the production of single chain antibodies, such as those described in U.S. Pat. No. 4,946,778 can also be adapted to produce single chain antibodies to the antigen of interest. Also, transgenic mice or other organisms, including other mammals, may be used to express humanized antibodies.

Antibodies obtained using the above methods may be used without further modification, or if desired following modification including conjugation to one or more reporter or effector molecules, for any suitable diagnostic or therapeutic purpose. An antibody, optionally conjugated to a therapeutic moiety, can be used therapeutically alone or in combination with a cytotoxic factor(s) and/or cytokine(s). In particular, antibodies can be conjugated to a therapeutic agent, such as a cytotoxic agent, a radionuclide or drug moiety to modify a given biological response. The therapeutic agent is not to be construed as limited to classical chemical therapeutic agents. For example, the therapeutic agent may be a drug moiety which may be a protein or polypeptide possessing a desired biological activity. Such moieties may include, for example and without limitation, a toxin such as abrin, ricin A, *pseudomonas* exotoxin, or diphtheria toxin, a protein such as tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Therapeutic agents also include cytotoxins or cytotoxic agents including any agent that is detrimental to (e.g. kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carnustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other therapeutic moieties may include radionuclides such as $^{111}$In and $^{90}$Y, $Lu^{177}$, $Bismuth^{213}$, $Californium^{252}$, Iridium$^{192}$ and Tunsten$^{188}$/Rhenium$^{188}$; or drugs such as but not limited to, alkylphosphocholines, topoisomerase I inhibitors, taxoids and suramin.

Techniques for conjugating such therapeutic agents to antibodies are well known in the art (see, e.g. Arnon et al., "Monoclonal Antibodies For Immunotargeting Of Drugs In Cancer Therapy", in Monoclonal Antibodies And Cancer Therapy, Reisfeld et al., eds., 1985 pp. 243-56, ed. Alan R. Liss, Inc; Hellstrom et al., "Antibodies For Drug Delivery", in Controlled Drug Delivery, 2nd Ed., Robinson et al., eds., 1987, pp. 623-53, Marcel Dekker, Inc.; Thorpe, "Antibody Carriers Of Cytotoxic Agents In Cancer Therapy: A Review", in Monoclonal Antibodies '84: Biological And Clinical Applications; Pinchera et al., 1985, eds., pp. 475-506; "Analysis, Results, And Future Prospective Of The Therapeutic Use Of Radiolabelled Antibody In Cancer Therapy", in Monoclonal Antibodies For Cancer Detection And Therapy, Baldwin et al. (eds.), 1985, pp. 303-16, Academic Press; Thorpe et al., 1982 "The Preparation And Cytotoxic Properties Of Antibody-Toxin Conjugates", Immunol. Rev., 62:119-58 and Dubowohik et al., 1999, Pharmacology and Therapeutics, 83, 67-123).

The antibodies for use in the invention include analogues and derivatives that are modified, for example but without limitation, by the covalent attachment of any type of molecule. Preferably, said attachment does not impair immunospecific binding. In one aspect, an antibody can be conjugated to a second antibody to form an antibody heteroconjugate (see U.S. Pat. No. 4,676,980).

In other embodiments, the invention provides the therapeutic use of fusion proteins of the antibodies (or functionally active fragments thereof), for example but without limitation, where the antibody or fragment thereof is fused via a covalent bond (e.g. a peptide bond), at optionally the N-terminus or the C-terminus, to an amino acid sequence of another protein (or portion thereof; preferably at least a 10, 20 or 50 amino acid portion of the protein). Preferably the antibody, or fragment thereof, is linked to the other protein at the N-terminus of the constant domain of the antibody. In another aspect, an antibody fusion protein may facilitate depletion or purification of a polypeptide as described herein, increase half-life in vivo, and enhance the delivery of an antigen across an epithelial barrier to the immune system.

Where the fusion protein is an antibody fragment linked to an effector or reporter molecule, this may be prepared by standard chemical or recombinant DNA procedures. For instance, it may have a macrocycle for chelating a heavy metal atom, or a toxin, such as ricin, attached to it by a covalent bridging structure. A preferred effector group is a polymer molecule, which may be attached to the modified Fab fragment to increase its half-life in vivo.

The polymer molecule may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly (ethyleneglycol) or derivatives thereof.

Particular naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 25000 to 40000 Da. The polymer size may in particular be selected on the basis of the intended use of the product. Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 25000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 25000 Da to about 40000 Da.

Each polymer molecule attached to the modified antibody fragment may be covalently linked to the sulphur atom of a cysteine residue located in the fragment. The covalent linkage will generally be a disulphide bond or, in particular, a sulphur-carbon bond.

Where desired, the antibody fragment may have one or more effector or reporter molecules attached to it. The effector or reporter molecules may be attached to the antibody fragment through any available amino acid side-chain or terminal amino acid functional group located in the fragment, for example any free amino, imino, hydroxyl or carboxyl group.

An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

Standard chemical or recombinant DNA procedures in which the antibody fragment is linked either directly or via a coupling agent to the effector or reporter molecule either before or after reaction with the activated polymer as appropriate may be used. Particular chemical procedures include, for example, those described in WO 93/06231, WO 92/22583, WO 90/09195, WO 89/01476, WO 99/15549 and WO03/031581. Alternatively, where the effector or reporter molecule is a protein or polypeptide the linkage may be achieved using recombinant DNA procedures, for example as described in WO 86/01533 and EP 0392745.

Most preferably antibodies are attached to poly(ethyleneglycol) (PEG) moieties. Preferably, a modified Fab fragment is PEGylated, i.e. has PEG (poly(ethyleneglycol)) covalently attached thereto, e.g. according to the method disclosed in EP 0948544 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one embodiment, a PEG modified Fab fragment has a maleimide group covalently linked to a single thiol group in a modified hinge region. A lysine residue may be covalently linked to the maleimide group. To each of the amine groups on the lysine residue may be attached a methoxypoly(ethyleneglycol) polymer having a molecular weight of approximately 20,000 Da. The total molecular weight of the entire effector molecule may therefore be approximately 40,000 Da.

Antibodies prepared directly or indirectly as a result of using the methods of the invention find use in the treatment and/or prophylaxis of a disease or condition depending on the antigen of interest selected. For example but without limitation, an antigen restricted to expression on the surface of tumour cells may be selected for immunisation of one or more animals.

Therefore, according to the invention provided is the use of an antibody prepared using the methods of the invention for the manufacture of a medicament for the treatment and/or prophylaxis of a condition or disease, for example but without limitation, cancers, autoimmune disorders or inflammatory disorders. Also provided is an antibody for use in therapy, for example therapy of a disease or condition such as cancers, autoimmune disorders or inflammatory disorders. For such use the antibodies will generally be administered in the form of a pharmaceutical composition.

Thus, according to the invention there is provided a pharmaceutical composition comprising an antibody which recognises an antigen of interest and a pharmaceutically acceptable diluent, excipient and/or carrier.

When a reference is made herein to a method of treating or preventing a disease or condition using a particular antibody or combination of antibodies, it is to be understood that such a reference is intended to include the use of that antibody or combination of antibodies in the preparation of a medicament for the treatment and/or prophylaxis of the disease or condition.

The composition will usually be supplied as part of a sterile, pharmaceutical composition that will normally include a pharmaceutically acceptable carrier. This composition may be in any suitable form (depending upon the desired method of administering it to a patient).

Antibodies of the invention may be administered to a subject by any of the routes conventionally used for drug administration, for example they may be administered parenterally, orally or by inhalation. The most suitable route for administration in any given case will depend on the particular antibody, the disease or condition involved, the subject, and the nature and severity of the disease or condition and the physical condition of the subject.

The antibodies may be administered in combination, e.g. simultaneously, sequentially or separately, with one or more other therapeutically active compounds, e.g. anti-tumour or anti-inflammatory compounds.

Pharmaceutical compositions may be conveniently presented in unit dose forms containing a predetermined amount of an antibody of the invention per dose. Such a unit may contain for example but without limitation, 750 mg/kg to 0.1 mg/kg depending on the condition being treated, the route of administration and the age, weight and condition of the subject.

Pharmaceutically acceptable carriers for use in the invention may take a wide variety of forms depending, e.g. on the route of administration.

Compositions for oral administration may be liquid or solid. Oral liquid preparations may be in the form of, for example, aqueous or oily suspensions, solutions, emulsions, syrups or elixirs, or may be presented as a dry product for reconstitution with water or other suitable vehicle before use. Oral liquid preparations may contain suspending agents as known in the art.

In the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are generally employed. In addition to the common dosage forms set out above, antibodies of the invention may also be administered by controlled release means and/or delivery devices. Tablets and capsules may comprise conventional carriers or excipients such as binding agents for example, syrup, acacia, gelatin, sorbitol, tragacanth, or polyvinylpyrrolidone; fillers, for example lactose, sugar, maize-starch, calcium phosphate, sorbitol or glycine; tableting lubricants, for example magnesium stearate, talc, polyethylene glycol or silica; disintegrants, for example potato starch; or acceptable wetting agents such as sodium lauryl sulphate. The tablets may be coated by standard aqueous or non-aqueous techniques according to methods well known in normal pharmaceutical practice.

Pharmaceutical compositions of the present invention suitable for oral administration may be presented as discrete units such as capsules, cachets or tablets, each containing a predetermined amount of the antibody, as a powder or granules, or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the antibody with the carrier, which constitutes one or more necessary ingredients. In general, the compositions are prepared by uniformly and intimately admixing the antibody with liquid carriers or finely divided solid carriers or both, and then, if necessary, shaping the product into the desired presentation. For example, a tablet may be prepared by compression or moulding, optionally with one or more accessory ingredients.

Pharmaceutical compositions suitable for parenteral administration may be prepared as solutions or suspensions of the antibodies of the invention in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include aqueous or non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. Extemporaneous injection solutions, dispersions and suspensions may be prepared from sterile powders, granules and tablets.

Pharmaceutical compositions can be administered with medical devices known in the art. For example, in a preferred embodiment, a pharmaceutical composition of the invention can be administered with a needleless hypodermic injection device, such as the devices disclosed in U.S. Pat. Nos. 5,399, 163; 5,383,851; 5,312,335; 5,064,413; 4,941,880; 4,790,824; or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicaments through the skin; U.S. Pat. No. 4,447, 233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the pharmaceutical compositions of the invention can be formulated to ensure proper distribution in vivo. For example, the blood-brain barrier excludes many highly hydrophilic compounds and it may be preferable to deliver pharmaceutical compositions in liposomes. Thus, in one embodiment of the invention, the antibodies of the invention are formulated in liposomes; in a more preferred embodiment, the liposomes include a targeting moiety. In a most preferred embodiment, the therapeutic compounds in the liposomes are delivered by bolus injection to a site proximal to the problem area, e.g. proximal to a tumour. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhancing targeted drug delivery (see, e.g. Ranade, V V. 1989, J. Clin. Pharmacol. 29:685). Exemplary targeting moieties include folate or biotin (see, e.g. U.S. Pat. No. 5,416,016); mannosides (Umezawa et al., 1988, Biochem. Biophys. Res. Commun. 153:1038); antibodies (Bloeman, P G. et al., 1995, FEBS Lett. 357:140; M. Owais et al., 1995, Antimicrob. Agents Chemother. 39:180); surfactant protein A receptor (Briscoe et al., 1995, Am. J. Physiol. 1233:134), different species of which may comprise the formulations of the inventions, as well as components of the invented molecules; p120 (Schreier et al., 1994, J. Biol. Chem. 269:9090); see also Keinanen, K. & Laukkanen, M L. 1994, FEBS Lett. 346:123; Killion, J J. & Fidler, U. 1994, Immunomethods 4:273. The compositions may be presented in unit-dose or multi-dose containers, for example in sealed ampoules and vials and to enhance stability, may be stored in a freeze-dried (lyophilized) condition requiring only the addition of the sterile liquid carrier, for example water for injections, immediately prior to use. The sterile liquid carrier may be supplied in a separate vial or ampoule and can be a solvent or dispersion medium containing, for example, water, ethanol, polyol (e.g. glycerol, propylene glycol and liquid polyethylene glycol), suitable mixtures thereof, and vegetable oils. Advantageously, agents such as a local anaesthetic, preservative and buffering agents can be included the sterile liquid carrier.

The dosage to be administered of an antibody will vary according to the particular antibody, the disease or condition involved, the subject, and the nature and severity of the disease and the physical condition of the subject, and the selected route of administration; the appropriate dosage can be readily determined by a person skilled in the art. For the treatment and/or prophylaxis of a disease or condition in humans and animals pharmaceutical compositions comprising antibodies can be administered to patients (e.g., human subjects) at therapeutically or prophylactically effective dosages (e.g. dosages which result in tumour growth inhibition and/or tumour cell migration inhibition) using any suitable route of administration, such as injection and other routes of administration known in the art for antibody-based clinical products.

The compositions may contain from 0.1% by weight, preferably from 10-60%, or more, by weight, of the antibody of the invention, depending on the method of administration.

It will be recognized by one of skill in the art that the optimal quantity and spacing of individual dosages of an antibody of the invention will be determined by the nature and extent of the disease or condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

Preferred features of each embodiment of the invention are as for each of the other embodiments mutatis mutandis. All publications, including but not limited to patents and patent applications cited in this specification are herein incorporated by reference as if each individual publication were specifically and individually indicated to be incorporated by reference herein as though fully set forth.

The invention will now be described with reference to the following examples, which are merely illustrative and should not in any way be construed as limiting the scope of the present invention.

EXPERIMENTAL

Five Sprague Dawley Rats were immunised with 10 µg recombinant human CSF-1 (Peprotech #300-25) in 200 µl, 50:50 complete Freund's adjuvant and Sterile PBS. The animals were then boosted at week 3 as before but using incomplete Freund's adjuvant and Sterile PBS. At week 6 the rats were given a third boost as for the second boost but in a 100 µl volume. A test bleed was taken and the sera analysed for neutralising activity in the M-NFS-60 proliferation assay (see below). The rats were boosted twice more before being sacrificed and the blood and spleens harvested for cell storage.

Preparation of Rat Lymphocytes and Splenocytes (the Populations for Enrichment)

Lymphocytes were separated from whole blood by firstly diluting the samples at approximately 1:10 in sterile PBS. Then 8 ml of diluted blood was layered onto 5 ml of Mammalian Lympholyte® (Cedarlane Laboratories Ltd.

CL5120) in 15 ml Falcon tubes. The samples were then centrifuge at 800 g for 20 min giving a well-defined, white lymphocyte layer at the interface between the liquids. This lymphocyte containing band and the upper 'blood plasma' containing layer were transferred into a new 15 ml Falcon tube and centrifuged at 800 g for 10 min to pellet the lymphocytes. The supernatant was collected and stored at 4° C. for future use, whilst the cells were washed 3 times in immune medium (RPMI, 10% FCS, 2% HEPES, 1% Glutamine, and 1× Pen/Strep). Following the final wash the cells were frozen in 90% FCS and 10% DMSO and stored in liquid nitrogen until use.

Individual rat spleens were transferred into warmed immune media and cut into small pieces. The pieces were pushed through a mesh strainer to disperse the splenocytes. These were pelleted by centrifugation, the supernatant was removed and the cells washed thoroughly in immune media. The cell pellets were frozen as stocks in 90% FCS and 10% DMSO aliquots and stored in liquid nitrogen until use.

Magnetic Separation

A series of magnetic enrichment steps were carried using the VarioMACS separation unit (Miltenybiotec #130-090-282), with the final step selecting for B cells specific for human CSF-1. The enrichment process was carried out using rat lymphocytes recovered from stocks taken from 5 animals immunised with human CSF-1. Upon defrosting and recovery in 37° C. pre-warmed media the cells were then cultured overnight in immune media (RPMI, 10% FCS, 2% HEPES, 1% Glutamine, and 1× Pen/Strep) before the separation procedure. Following the culture step the lymphocytes were washed thoroughly with cold PBS before being counted (total $2.9 \times 10^7$ cells) and resuspended in 800 µl of filter sterilised sort buffer (0.5% BSA, 2 mM EDTA in PBS).

The first step of the enrichment process was the depletion the T cell population from the lymphocytes using a pan T cell micro-bead kit, specific for rat OX52 (Miltenybiotec #130-090-320). The kit was used as described by the manufacturer, with 800 µl of readily prepared anti-OX52 coated beads added per $10^7$ cells. The cell/bead mix was placed in the fridge for 15 min to incubate. Following this incubation the cells were washed twice with 50 ml cold sort buffer to remove any unbound beads. After the final wash, the cells were resuspended in 5 ml cold sort buffer and filtered using pre-separation filter (Miltenybiotec #130-041-407). The cells were then loaded on to a pre-washed LS separation column (Miltenybiotec #130-042-401). The flow though was collected and the column was washed with 2×5 ml cold sort buffer which was also collected; all the material that remained bound to the column was discarded. The flow through and the wash were combined and centrifuged to pellet the cells. The cells were then resuspended in 15 ml sort buffer and washed and counted ($2.5 \times 10^7$ cells) for the next step in the procedure.

Non-specific depletion was performed to remove any B cells that had bound non-specifically to components of the final sort other than human CSF-1. The cells were resuspended in 2 ml sort buffer with 10 µg/ml biotinylated goat anti-human CSF-1 (R&D Systems #BAF 216) and incubated in the fridge for 30 min. Following this incubation the cells were washed twice with 50 ml cold sort buffer and centrifuged. The cell pellet was resuspended in 90 µl of cold sort buffer and 10 µl of Streptavidin coated MACS beads Miltenybiotec #130-048-101) per $10^7$ cells. The cells were then incubated in the fridge for 15 min. Again following the incubation step the cells were washed twice with 50 ml cold sort buffer before being resuspended in 5 ml of the sort buffer for loading on to a pre-washed LS column for sorting. The flow through was collected, as was the 2×5 ml washed with cold sort buffer.

The cells from the flow though and washes were centrifuged, washed in sort buffer and counted ($1.35 \times 10^7$ cells) before being resuspended in 2 ml of sort buffer. A mix of biotinylated goat anti-human CSF-1 (R & D Systems #BAF 216) at a final concentration of 5 µg/ml and human CSF-1 (Peprotech # 300-25), final concentration 2 µg/ml were added to the cells and the mix was incubated for 30 min in the fridge. The cells were then washed 3 times in cold sort buffer, resuspended in 90 µl of sort buffer and 10 µl Streptavidin coated MACS beads per $10^7$ cells and incubated in the fridge for 15 min. The cells were then washed 3 times in 50 ml sort buffer and resuspended in 5 ml cold sort buffer before loading onto a pre-washed LS column. The first 5 ml flow through was collected for testing for CSF-1 specific antibody production. The column was washed 4 times with 8 ml of sort buffer. After the final wash the LS column was removed from the VarioMACS seperation unit and the cells were eluted in sort buffer. The cells were then counted ($2.45 \times 10^5$ cells) and then washed before being added to the culture mix.

Plating and Culture

The human CSF-1 specific B cells sorted on the magnetic column were seeded at approximately 100 cells per well across 20×96-well tissue in B cell stimulating culture mix consisting of 50,000 irradiated EL4.B5 cells and 4% rabbit TSN (rabbit T cells stimulated culture supernatant) in a total volume of 200 µl per well. The cells were cultured for 7 days before the culture supernatant was assayed for human CSF-1 specific antibody secretion.

FLISA on Indirectly Captured Human CSF-1

SuperAvidin™ Coated Microspheres (Bangs Laboratories, Inc. # CPO1N) were coated with human CSF-1 indirectly by capturing the protein using a biotinylated polyclonal anti-human CSF-1 (R&D Systems #BAF 216). Approximately 50 µl was used per 384-well assay plate (FMAT #). For 5×384-well assay plates a total of 250 µl of undiluted beads were used. The coating was a one step process with 250 µl beads, 12.5 µg biotinylated polyclonal anti-human CSF-1 and 20 µg human CSF-1 (Peprotech #300-25) incubated overnight at 4° C. in a total volume of 15 ml PBS. Following overnight incubation the beads were washed in 3×15 ml PBS and were then ready for use in the assay.

Figure 1:
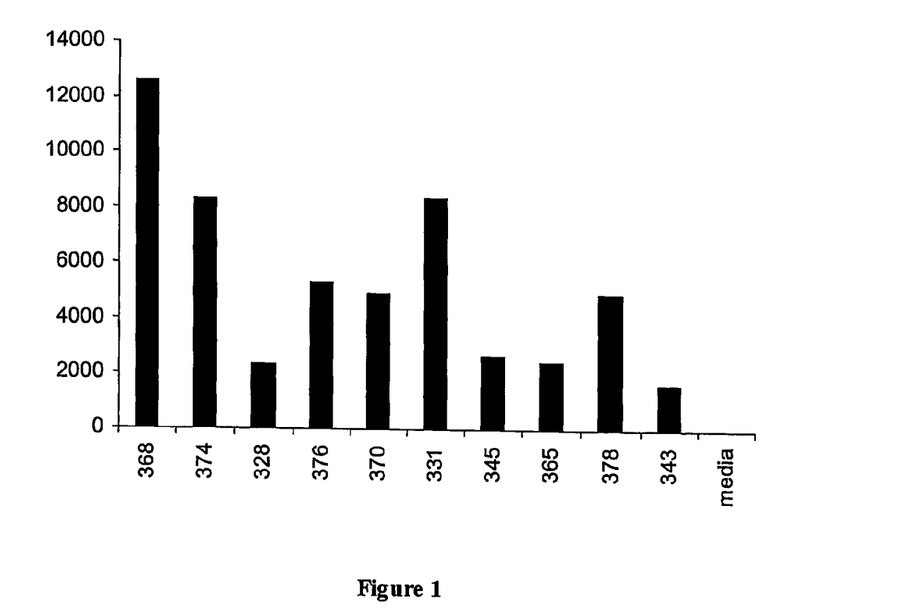
FIG. 1 is a histogram showing results obtained by fluorescence-linked immunosorbent assay (FLISA). Number labels indicate those wells containing culture supernatant for assay. A negative control containing media in place of culture supernatant is also shown.

10 µl of undiluted B cell supernatant was transferred to a 384-well plate, before adding a 20 µl mix of Cy-5 and human CSF-1 coated beads in PEG block (1% PEG MW 20000, 0.1% Tween in PBS). The Cy5-conjugated $F(ab')_2$ fragment Goat anti-Rat IgG, Fcγ fragment specific (Jackson ImmunoResearch 112-066-071) was used at a starting concentration of 1:5000 and the human CSF-1 coated beads (approximately 50 µl of undiluted beads was used per 384-well plate) were plated to give a density of approximately 2000 beads per well. The plate was incubated at room temperature in the dark for 1½ hours until beads settled before being read using the Wang Goldman model on the '8200 Cellular detection system' using the 8200 Analysis Software (Applied Biosystems). The data was read from the FL1 channel with a size gating to remove any non-specific noise from these readings. FIG. 1 shows ten culture supernatants containing anti-CSF-1 antibodies.

CSF-1 Dependent M-NFS-60 Proliferation Assay

Figure 2:
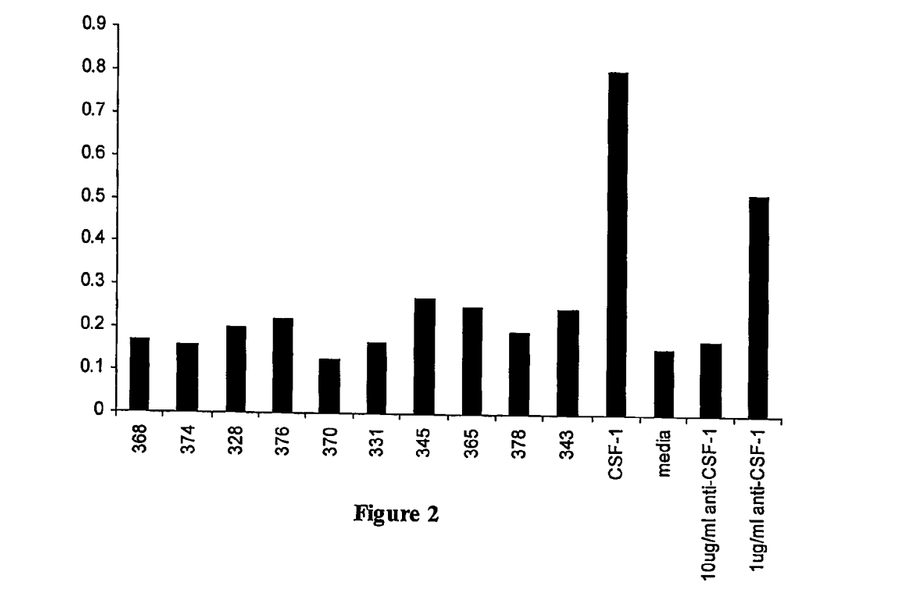
FIG. 2 is a histogram showing inhibition of cell proliferation by anti-CSF-1 antibodies present in culture supernatant. All wells contain 20 ng/ml CSF-1 with the exception of the negative control (labelled media). Number labels indicate those wells containing culture supernatant for assay. Controls include a positive showing stimulation of proliferation in the presence of CSF-1, and inhibition of proliferation in the presence of anti-CSF-1 antibody at 1 µg/ml and 10 µg/ml.

M-NFS-60 cells were seeded across a 96-well plate in a 50 ml volume at a concentration of $2 \times 10^5$ cells/ml ($10^4$ cells per well). 50 µl of B cell culture supernatant (above) was added and the cells and antibody containing supernatant were incubated in the absence of human CSF-1 for 30 min at 37° C. The human CSF-1 was prepared in immune media at a stock concentration of 200 ng/ml; 10 μl of this stock was added to each of the wells to give a final concentration of 20 ng/ml. The M-NFS-60 cell assay was then left to incubate for 96 hr. The inhibition of cell proliferation by antibody neutralisation of the CSF-1 was measured using the CellTiter 96® AQueous One Solution Reagent (Promega G358A). 20 μl of proliferation substrate was added to each of the wells and the plates were incubated for a further 4 hr. Each plate was set up with controls: a negative control with no CSF-1, a positive control with 20 ng/ml CSF-1, and inhibition controls with varying concentrations (from 1 μg/ml to 10 μg/ml) of an anti-mouse CSF-1 neutralising antibody (R&D Systems #AF416). The plates were read on a Multiskan (Labsystems) plate reader at 492 nm and Ascent software was used for data analysis. FIG. 2 shows ten culture supernatants containing antibodies capable of neutralising CSF-1 stimulated cell proliferation.

The invention claimed is:

1. The method of obtaining from a population of cells those cells which produce an antibody which recognises an antigen of interest, said method comprising:
   a) bringing into contact:
      i) a population of cells at least one of which is capable of producing an antibody;
      ii) an antigen of interest;
      iii) a polyclonal antibody-particle complex wherein said polyclonal antibody recognises an antigen of interest and said particle comprises a magnetic bead enabling recovery of said complex;
      wherein parts i) to iii) are performed simultaneously; and
   b) recovering from the population, those cells associated with the antibody-particle complex.

2. A method of isolating an antibody which recognises an antigen of interest comprising:
   a) bringing into contact:
      i) a population of cells at least one of which is capable of producing an antibody;
      ii) an antigen of interest;
      iii) a polyclonal antibody-particle complex wherein said polyclonal antibody recognises an antigen of interest and said particle comprises a magnetic bead enabling recovery of said complex;
      wherein parts i) to iii) are performed simultaneously,
   b) recovering from the population, those cells associated with the antibody-particle complex;
   c) culturing a plurality of those cells associated with the antigen-antibody-particle complex;
   d) screening the cultured cells to identify those cells capable of producing an antibody which recognises an antigen of interest; and
   e) isolating said antibody directly or indirectly from the cells.

* * * * *